United States Patent [19]
Rudloff

[11] Patent Number: 6,010,507

[45] Date of Patent: Jan. 4, 2000

[54] REPAIR OF BONE FRACTURE USING FLEXIBLE FULLY OR PARTIALLY CANNULATED COMPRESSION/ DECOMPRESSION FIXATION ELEMENT

[76] Inventor: David A. C. Rudloff, 3400 N. Riverside Dr., Indialantic, Fla. 32903

[21] Appl. No.: 09/122,158

[22] Filed: Jul. 24, 1998

[51] Int. Cl.[7] .................................................... A61B 17/58
[52] U.S. Cl. .................................. 606/72; 606/73; 606/77
[58] Field of Search ................................ 606/72, 73, 76, 606/77, 78

[56] References Cited

U.S. PATENT DOCUMENTS

| | | | |
|---|---|---|---|
| 5,716,358 | 2/1998 | Ochoa et al. .............................. | 606/72 |
| 5,893,850 | 4/1999 | Cachia ...................................... | 606/72 |

*Primary Examiner*—Michael Buiz
*Assistant Examiner*—Julian W. Woo
*Attorney, Agent, or Firm*—Charles E. Wands

[57] ABSTRACT

A bone fracture is repaired using a flexible, resorbable cannulated, self-tapping (in soft bone) compression and decompression fixation element to retain respective sections of bone in a spatial relationship that facilitates mending with minimal or no compression, that might otherwise lead to collapse and/or misalignment of the bone sections. The fixation element is inserted through a first bone section and intersects a second bone section at an acute angle relative to the fracture. As the fixation element is driven into the second bone section, its elasticity stably secures the mutually facing surfaces of the two bone sections in a mending position. Since the fixation element is flexible, its forward end may be deflected when it encounters the sidewall of the second bone section. This deflection imparts a torquing force, which urges the first bone section away from the fracture joint, thereby off-loading the compression force the fixation element naturally imparts, as it is self-tapped into the soft portion of the second sections of bone. The fixation element is then adjusted so that the two opposing bone sections optimally just touch one another, allowing the fracture to mend, sometimes using resistance against a medullary block such as a transverse pin or graft. The fixation element's resorbable material is eventually replaced by bone tissue as the two bone sections grow together.

20 Claims, 3 Drawing Sheets

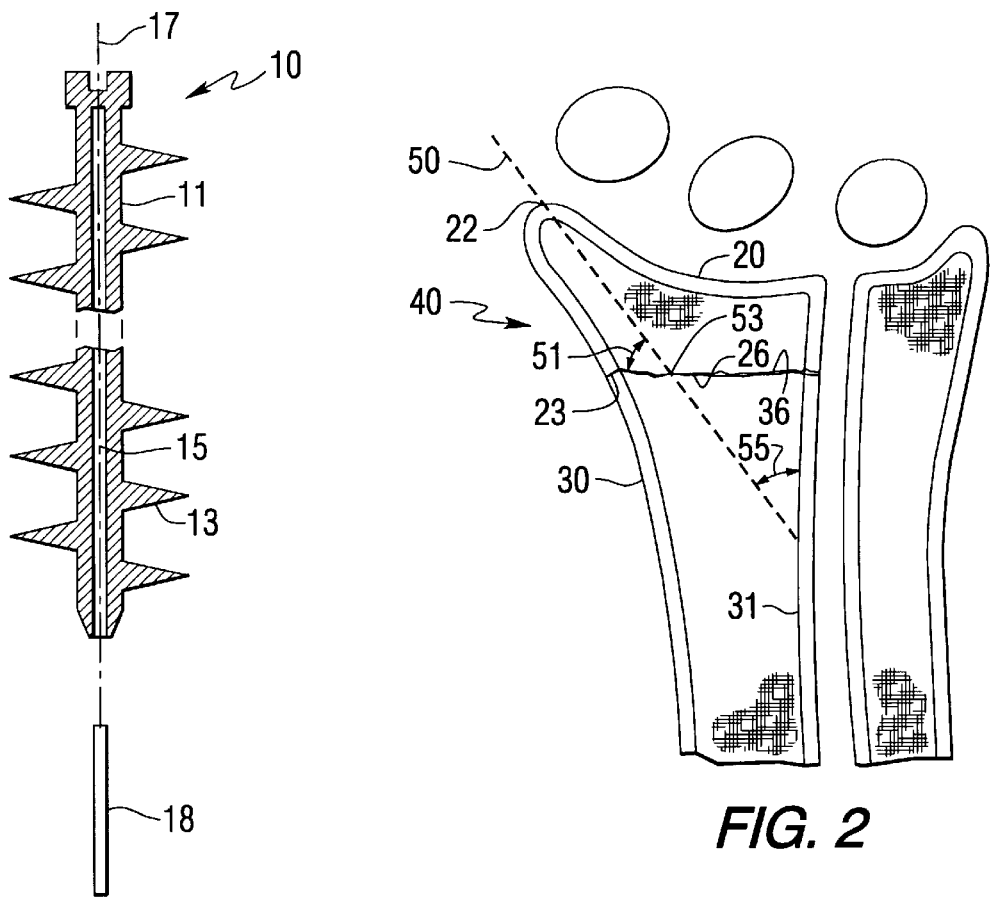
FIG. 1
FIG. 2
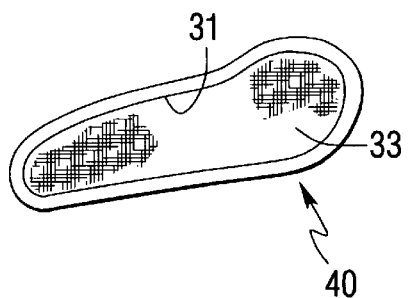
FIG. 3
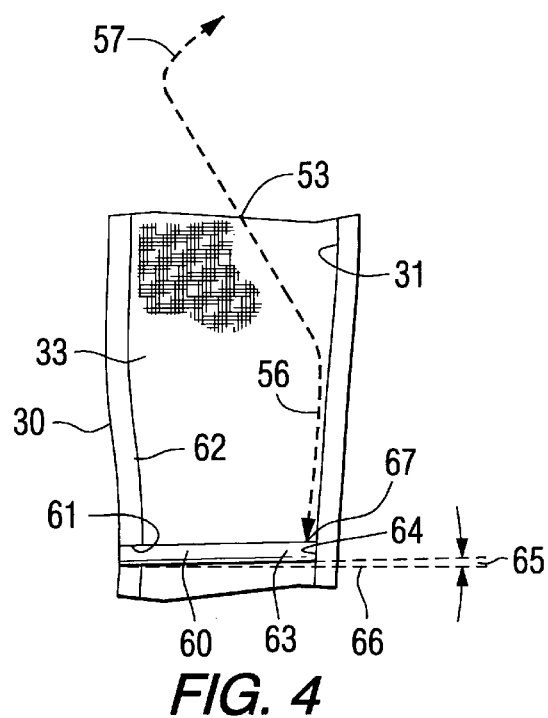
FIG. 4

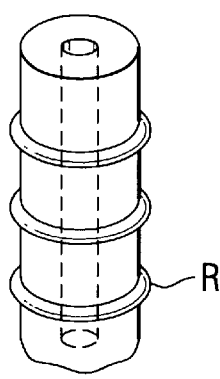
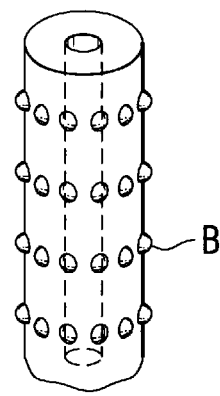
FIG. 1B  FIG. 1C
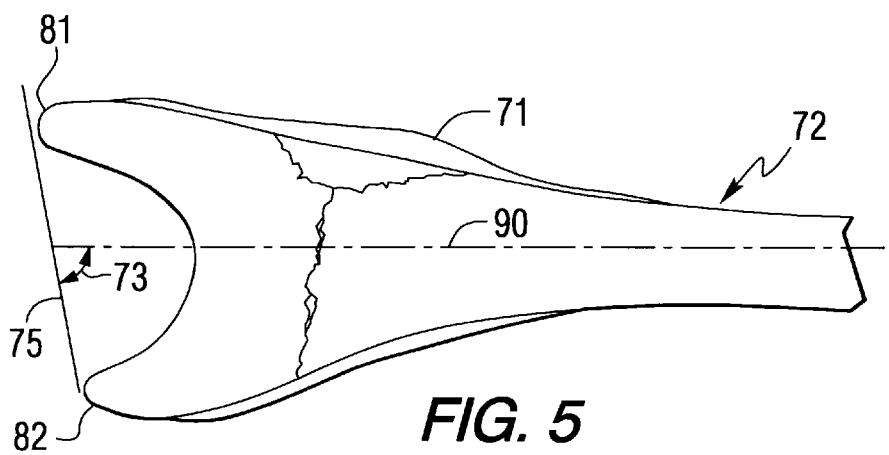
FIG. 5
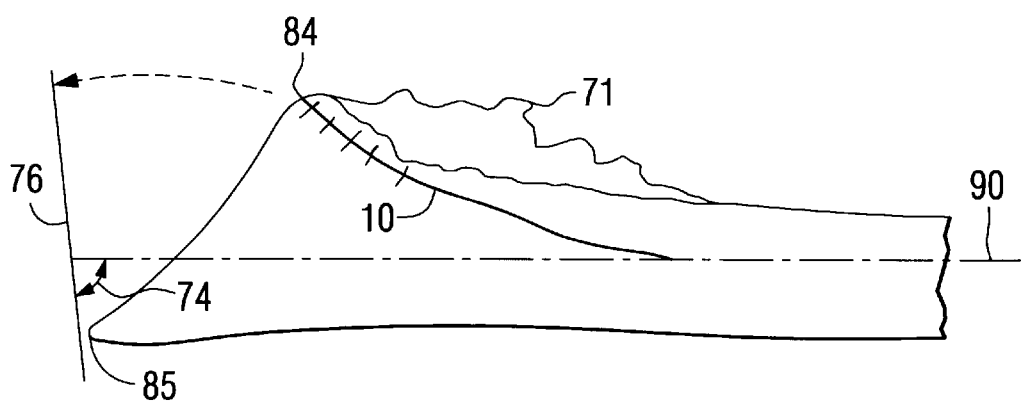
FIG. 6

REPAIR OF BONE FRACTURE USING FLEXIBLE FULLY OR PARTIALLY CANNULATED COMPRESSION/ DECOMPRESSION FIXATION ELEMENT

FIELD OF THE INVENTION

The present invention relates in general to the repair and reconstruction of bone fractures, and is particularly directed to a new and improved procedure and associated orthopaedic surgical appliance for stably retaining respective sections of bone in place. The appliance comprises a flexible and resorbable cannulated compression and decompression textured surface fixation element, such as a screw, ridged nail, pin and the like, that facilitates mending of the fracture. This textured fixation element is inserted into sections of bone along a path that acts to flex or bias the fixation element transverse to its longitudinal axis, so as to oppose undesirable compression between the stabilized bone sections.

BACKGROUND OF THE INVENTION

A variety of bone attachment devices (such as (Py-Desmonet) stainless steel pins, (Elder and Rush) rods, screws, plates and the like) is currently available to orthopaedic surgeons for securing sections of bone in place, in the course of repair, reconstruction, etc., of a fracture. However, since not every bone has the same physical geometry or interior characteristics, not every device is suitable for any application. Also, the use of some devices may eventually lead to further problems, such as infections, where the securing device extends through the skin tissue, or an osteoporotic condition where the securing device places or allows thin walled bones in compression at the fracture joint, angling or shortening the bone ("malunion").

SUMMARY OF THE INVENTION

In accordance with the present invention, problems associated with conventional bone attachment devices and their customary use, such as but not limited to those described above, are effectively obviated by a new and improved procedure for the repair and reconstruction of bone fractures, that preferably employs a compression and decompression, generally longitudinal textured fixation element such as, but not limited to a partially self-tapping screw, ridged rod, nail, pin and the like, made of FDA-approved resorbable material, that is both flexible and cannulated.

Once it has been inserted into adjacent sections of bone, the fixation element securely retains the bone sections in a stable spatial relationship, so as to facilitate mending of the fracture with effectively minimal or no compression, that might otherwise lead to collapse of the bone sections. Although the fixation element may be made of non-resorbable material, to be removed subsequent to mending of the fracture, it is preferably made of a material, such as polylactic acid, that is readily resorbed into the bone, as it is eventually replaced by bone tissue in the course of the two bone sections growing together.

The resorbable cannulated compression and decompression fixation element is inserted at a location of a first bone section, that facilitates entry of the fixation element in an orientation generally orthogonal to the surface of the sidewall of the first bone section. In order to ensure that the fixation element conforms with a prescribed bone-stabilizing orientation, a flexible guide pin, along which the cannulated fixation element travels, may be initially inserted into the bone sections along the intended orientation geometry. This also facilitates having the fixation element travel along an initially generally linear insertion path through the first bone section and intersecting the second bone section at an acute angle relative to the fracture.

As the fixation element is driven into the second bone section, its inherent compression and decompression geometry secures the mutually facing surfaces of the two bone sections in a stabilized mending position by placing tension on the surrounding attached soft tissue envelope. At the surgeon's election, the two sections of bone may not be placed under longitudinal compressive load, since compressive loading may cause misalignment, longitudinal shortening or tilting or side slippage of the two comminuted (fragmented) bone sections, that would lead to malunion. Also, excessive compression may cause either or both of the sections of bone to displace.

The acute angle and location where the fixation element intersects the fracture are selected such that further insertion/travel of the fixation element into the second bone section brings the forward end of the fixation element into an acute angle engagement with an interior sidewall of the second bone section, at the surgeon's election. Since the fixation element is flexible, its forward end may be deflected along an interior sidewall region of the second bone section's medullary section. This deflection of the forward end of the fixation element imparts a biasing or torquing force, which urges the first bone section away from compression of the fracture joint with the second bone section, thereby off-loading the compression force the fixation element naturally imparts, as it is self-tapped into the bone. The non-smooth or textured surface of the fixation element (such as threads, ridges, bumps, and the like) assist in maintaining the fixation element in the desired fragment position.

The degree to which the deflection bias against the head end of the fixation element and thereby the attached first section of bone counteracts the inherent compression action of the attached muscles may be adjusted by inserting one or more fixation elements and controlling in-situ parameters. Once the fixation element has been driven through the first bone section and into the second bone section, and begins to undergo deflection as a result of its engagement with the latter's interior sidewall, the fixation element is adjusted so as to cause the two opposing bone sections to optimally 'slightly touch' one another. Such stable touching or approximate touching is frequently all that is necessary for a fracture to mend (especially metaphyseal). In essence, the "soft-tissue sleeve or envelope" of connective tissue attachments to the fragments is tightened, further maintaining relative fragment positions.

An impediment, in the form of a relatively small transversely extending pin, bone graft, rod or the like may be inserted through a hole drilled through a wall region of the bone section, such that a forward end of the rod or pin abuts against and is thereby 'leveraged off' the transverse abutment pin installed within the second bone section. The transverse abutment pin may be inserted so that it is oriented at an angle with the interior sidewall of the bone section, and is therefore effectively 'wedged' against the interior wall of the bone section by impingement of the forwardmost end of the fixation element.

This impeding of the depth of insertion of the forward end of the fixation element, in combination with the acute angle of the inserted pin or other device or substance (graft) in the medullary cavity, allows that portion of the fixation element affixed within the first bone section, and thereby the first bone section itself, to be torqued or 'jacked' away from the fracture joint, so as to decompress, off-load or relieve/resist excessive compression between the two bone sections.

The problem that resorbable material is expensive, and unused lengths of such material cannot be effectively reclaimed in a cost effective manner is solved by a further feature of the invention, in which the cannulated fixation element is formed as a relatively long section of resorbable material, that allows an unused portion of the fixation element to be retained for use in one or more additional procedures. For this purpose, the head end of the resorbable cannulated fixation element is configured to be readily grippable or engageable by hand or a tool, such as in the form of a flared wing or fin, or a generally regular polygon shape.

In accordance with its intended use, as the head end of the fixation element is rotated about the longitudinal axis of the fixation element, the resulting torsion force serves to rotate the forward or nose end of the cannulated fixation element about its longitudinal axis, and thereby rotationally 'thread' the fixation element along the guide pin passing through interior bore of the fixation element, and into the bone section. However, because of the resistance against the fixation element being imparted by the bone, there tends to be a build up of a torsion spring force within the fixation element at its point of entry into the bone section.

To counter this problem a chuck may be secured to a location along the fixation element where the fixation element enters the bone section. The chuck is configured to be readily gripped and rotated by the surgeon, so that both ends of the cannulated fixation element may be rotated together, reducing the build up of torsion spring forces along the length of the fixation element outside the bone. The use of a releasable chuck allows the chuck to be securely closed about the fixation element, used to rotationally insert the fixation element into the bone, and then released and repositioned for further use with the same length of the fixation element. Once the fixation element has been inserted to its desired depth into the bone and stably positioned, the unused portion of the fixation element is readily severed at its forwardmost end.

The extent that the fixation has useful length allows the remaining length of the fixation element, including the grippable head end to be employed for another fracture-mending procedure. In addition, configuring the surfaces of the semi-cylindrical depressions of the two plates of the chuck as threaded surfaces allows the chuck to be used to 'rethread' a fixation element, as desired. Thus, the longitudinal, textured fixation element can be cut to appropriate lengths at bone surface level, allowing its use in areas previously restricted by overlying vital soft tissue structures (e.g. tendon bone beds, or ligament and capsular attachment points). Such bone growth may be modified further by commercial or autograft additions of substances designed to promote such growth.

BRIEF DESCRIPTION OF THE DRAWINGS

FIG. 1 diagrammatically illustrates a flexible resorbable self-tapping cannulated compression decompression fixation element used for bone fracture repair;

FIG. 2 diagrammatically illustrates a fracture between a first bone section and a second bone section at an end metaphyseal bone region of a human radius;

FIG. 3 diagrammatically illustrates the cross-section of the fracture of the radius of FIG. 2;

FIG. 4 diagrammatically illustrates the deflected travel path of a flexible fixation element in the second bone section of FIG. 2;

FIGS. 5 and 6 are respective side and top views of the soft tissue envelope around a radius bone fracture;

DETAILED DESCRIPTION

Figure 7:
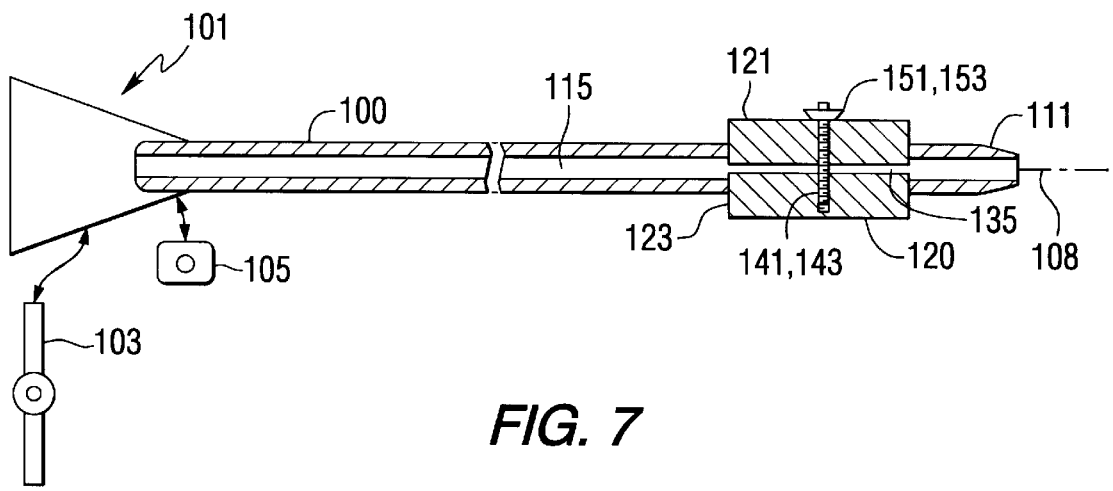
FIG. 7 diagrammatically illustrates a cannulated fixation element as a relatively long section of resorbable material.

In order to facilitate an understanding of the bone fracture repair methodology of the present invention, the application of the invention to the repair of a fracture at a metaphyseal region of a bone, in particular the metaphyseal regions of the radius and ulna bones at the human wrist joint, will be described. It is to be understood, however, that the case of the human wrist is given only as a non-limiting example. The present invention has application to fractures of other human bones that are configured to readily accommodate the procedure herein described, as well as in veterinary medicine.

As pointed out briefly above, the bone fracture repair methodology of the present invention uses an FDA-approved, commercially available, flexible and resorbable fixation element, preferably in the form of a cannulated, self-tapping cannulated compression decompression rod-shaped element, having a non-smooth or textured surface, such as a screw, ridged nail, pin, and the like. Such a textured fixation element is mechanically biased by the path along which it is inserted into the bone sections to be repaired, so as to retain the respective sections of bone in a spatial relationship that facilitates mending of the fracture with effectively minimal or no compression, thereby preventing collapse of the bone sections.

FIG. 1 diagrammatically illustrates a non-limiting example of such a generally longitudinal, textured fixation element in the form of a cannulated flexible screw 10, having a generally longitudinal shaft portion 11 from which a helically shaped threaded portion 13 radially projects. It is to be observed, however, that the fixation element may have a variety of structurally and functionally equivalent configurations, in addition to that of the illustrated threaded screw, such as, but not limited to a longitudinal rod, shaft, nail, pin and the like, having a surface which is sufficiently 'textured'.

By sufficiently 'textured' is meant a surface that causes the fixation element to maintain a prescribed impingement upon the bone sections, to prevent the fixation element from slipping or being displaced from an established insertion location and orientation within the bone sections, so that the intended mending bias is not compromised. For this purpose, rather than being threaded, as in FIG. 1, the surface of the flexible longitudinal fixation element may have a plurality of raised bumps, such as those diagrammatically illustrated at B in FIG. 1A, or raised circular ridges or rings, such as those diagrammatically illustrated at R in FIG. 1B, as non-limiting examples.

As pointed out earlier, the flexible longitudinal fixation element is preferably made of a polylactic acid-based material, that gradually resorbs upon contact with body fluid. As further shown in FIG. 1, the longitudinal shaft portion 11 of the fixation element may include an interior hollow bore 15 extending along a longitudinal axis 17, which not only enhances the flexibility of the fixation element 10, but allows it to travel along a precursor guide pin, such as a smooth stainless steel guide pin, shown at 18. Such a guide pin 18 is sized to pass through the hollow bore 15 of the fixation element, so that the fixation element 10 may effectively 'ride' along the guide pin, and thereby follow a prescribed path, such as a curvilinear path through the bone sections, at the surgeon's election.

FIG. 2 diagrammatically illustrates a fracture 23 between a first, or 'attached', end radius bone section 20 and a second, or 'target' main radius bone section 30, respectively, at an end metaphyseal bone region 41 of a human radius 40. FIG. 3 diagrammatically illustrates the cross-section of the radius 40 at the fracture 23. In order to secure the end radius bone section 20 to the main radius section 30, the textured surface fixation element, a cannulated flexible compression screw 10 of FIG. 1 in the present example, is initially inserted (riding along a guide pin) at a location 22 of the end radius section 20 that facilitates entry of the fixation element—at an orientation that is generally orthogonal to the surface of the relatively thin bone sidewall 24 of the end bone section 20.

This also allows the screw 10 to travel along an initially generally linear insertion path 50 through the end bone section 20, and intersecting the main radius section 30 at an acute angle 51 to the fracture 23 therebetween. As the screw 10 is driven from the end bone section 20 into the main radius section 30, its inherent compression and decompression functionality serves to stably hold the mutually facing surfaces 26 and 36 of the two opposing sections of radius bone 20 and 30, respectively, at length, in contact with, or 'touching' one another at the fracture 23 therebetween, bound by soft tissue attachments or other substances or devices, so that they will bond or grow together as the fracture mends.

It should be noted that it is not only not necessary, but frequently quite undesirable that the two comminuted, sometimes thin-walled sections of radius bone be placed under compressive load, which causes them to be or 'pushed' together. As noted earlier, compression loading can cause misalignment, crushing or side slippage of the two bone sections, so that one or both of the two bone sections engage or rub against other bones and shorten. This eventually leads to a malunion condition at the point of impingement impairing function in nearby joints. In addition, compression may cause either or both of the sections of bone (which in the case of the radius of the present example shown in FIG. 3 are relatively thin walled and therefore fragile) to fail or collapse or cave in to one another.

The acute angle 51 and location 53 where the screw 10 intersects the fracture 23 are selected such that further insertion/travel of the screw 10 into the main radius bone section 30 along path 50 will bring the forwardmost end point of the fixation element 10 into engagement at a relatively small acute angle 55 with an interior sidewall 31 of the main radius section 30. Also, as shown in FIG. 4, an impediment, in the form of a relatively small transversely extending pin, screw, bone graft, rod or the like (such as a 2 mm diameter resorbable rod) 60, may be inserted through a hole 61 drilled through opposite wall region 62 of the main radius bone section 30, such that a forward end 63 of the rod 60 abuts against location 64 at the interior sidewall 31 of main radius bone section 30.

The transverse abutment pin 60 may be inserted so that it is oriented at a slight acute angle 65 relative to a normal 66 with the interior sidewall 31 of the bone section, and is therefore effectively 'wedged' against the interior wall of the bone section by impingement of the forwardmost end or point of the fixation element 10 at a location 67 of the transverse pin 60. As a result of limiting or impeding the depth of insertion of the forward end of the fixation element, in combination with the acute angle 51 of the inserted pin or other device or substance (graft) in the medullary cavity allows that portion of the fixation element 10 that is affixed within the first bone section 20, and thereby the first bone section itself, to be torqued or 'jacked' away from the fracture joint 23, so as to decompress, off-load or relieve/resist excessive compression between the two bone sections.

More particularly, because the cannulated screw 10 is flexible and its insertion path at the surgeon's election 50 intersects the interior sidewall 31 of the main radius bone section 30 at acute angle 55, rather than continuing along a rectilinear path through the sidewall 31, the forward end of the cannulated fixation element is deflected or bent, so that it now follows a deflected path 56 along the interior sidewall 31 through the tissue region 33 of the main radius section 30. This deflection of the forward end of the fixation element imparts a biasing or torquing force, shown by arrow 57 in FIG. 4, which serves to urge the first bone section 20 away from the fracture joint 23, in opposition to the compression force naturally imparted by the soft tissue envelope between the two bone sections 20 and 30, as the fixation element 10 is inserted into the two sections of bone.

At the surgeon's election, the degree to which the deflection bias against the head end of the fixation element and thereby the attached section of bone counteracts the inherent action of the fixation element may be adjusted by controlling one or more parameters. Such parameters may include where the break occurs, the types and sizes of the bone sections, the size of the fixation element being used, the coefficient of elasticity of the fixation element material, the differential lengths of the fixation element in the attached bone section, the degree of threading or ridging or texture in the device, and the target bone section (which are based upon the length of the fixation element, per se, and the associated depth to which the fixation element is inserted into the target bone section), the location where the fixation element intersects the fracture, the angle at which the fixation element intersects the fracture, its deflection angle with the target bone sidewall, and its interaction with pins or material inserted across or into the medullary cavity.

What is important is, once the fixation element has been driven through the attached bone section and into the target bone section and begins to undergo deflection as a result of its engagement with the interior sidewall of the target bone section or the created intramedullary impediment or resistance by pin, graft of bone, bone substitute or other device or substance, the fixation element is adjusted (e.g., rotationally), so as to cause the two opposing bone sections to optimally 'slightly touch' one another opposing the natural tendency of the fragments to compress into deformity, while tightening the "soft tissue sleeve" of tissue around and attached to the fragments, thus maintaining fragment relationships, or it may penetrate the second fragment, at the surgeon's election.

The respective side and top views of FIGS. 5 and 6 diagrammatically illustrate such 'tightening' of the soft tissue envelope 71 around a radius bone 72 to restore both the tissue and bone to their pre-injury lengths and configurations, where the respective angles 73, 74 of lines 75 and 76 between end regions 81 and 82, 84 and 85 of the radius bone 72 are returned to within prescribed ranges of incidence (e.g., 8–15°) with the longitudinal axis 90 of the radius.

As described briefly above, resorbable material is expensive, and unused lengths of such material, such as may be configured in the forma of a cannulated screw, described above, cannot be effectively reclaimed in a cost effective manner. In accordance with a further feature of the invention, this problem is substantially reduced, by providing the cannulated fixation element as a relatively long section of resorbable material, in a configuration such as diagrammatically illustrated in FIG. 7, that allows an unused portion of the fixation element to be retained for use in one or more additional procedures.

For this purpose, the head or rearward end 101 of a resorbable cannulated or bored rod-shaped element 100 is configured to be readily grippable or engageable by hand or a tool, such as in the form of a flared wing or fin, shown at 103, or a generally regular polygon shape, shown at 105. As the head end 101 of the rod 100 is rotated about the longitudinal axis 108 of the rod, the resulting torsion force will rotate the forward or nose end 111 of the cannulated rod 100 about the axis 108, and thereby rotationally urge or 'thread' the rod-shaped fixation element 100 along the guide rod passing through interior bore 115 of the fixation element 100, and into the bone section.

Figure 8:
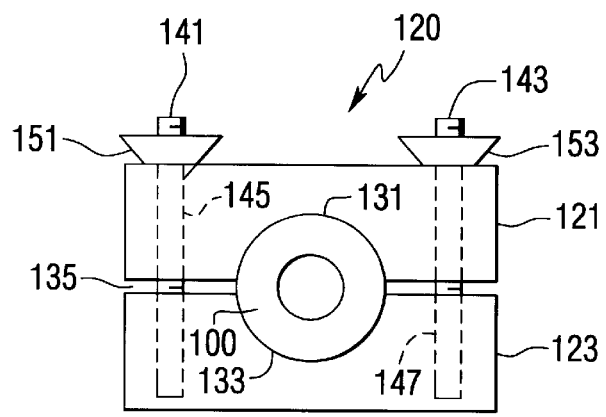
FIG. 8 is an end view of a chuck that is securable to a location along the fixation element of FIG. 7.

However, because of the resistance against the fixation element being imparted by the bone, there tends to be a build up of a torsion spring force-accumulated material fatigue within the fixation element at its point of entry into the bone section. Namely, twisting the head end 101, per se, of the fixation element 100 will not be reflected in a corresponding rotation of the entirety of the fixation element, which can lead to repetitive stress fatigue destruction of the fixation element. To counter this problem a chuck 120, such as that shown in detail in the end view of FIG. 8, is secured to a location along the fixation element where the fixation element enters the bone section. The chuck is configured to be readily gripped and rotated by the surgeon, so that both ends of the cannulated fixation may be rotated together, reducing the build up of torsion spring fatigue forces in the length of the fixation outside the bone.

As shown in FIG. 7 and in greater detail in FIG. 8, the chuck 120 may comprise a pair of chuck half-plates 121 and 123, having semi-cylindrical depressions 131 and 133 that are sized to readily receive and generally surround the outer diameter of the cannulated rod-shaped fixation element, leaving a very narrow kerf 135 therebetween. A plurality of tightening elements, such as threaded rods 141 and 143 passing through threaded bores 145 and 147, and having tightening screws 151 and 153 to securely, but releasably, join the two chuck half-plates 121 and 123 together about a desired location of the rod-shaped fixation element 100.

Once so tightened around the rod-shaped fixation element, the chuck facilitates rotation of the forward end of the fixation element by the surgeon, so that the entire external (to the bone) length of the cannulated fixation element may be rotated, reducing the build up of torsion spring forces along the length of the fixation element outside the bone, as described above. The use of a releasable chuck allows the chuck to be securely closed about the fixation element, used to rotationally insert the fixation element into the bone, and then released and repositioned for further use with the same length of fixation element. Once the fixation element has been inserted to its desired depth into the bone and stably positioned (e.g., via the fracture jack positioning procedure, described above), the unused portion of the fixation element is readily severed at its forwardmost end.

The extent that the generally longitudinally shaped fixation has useful length allows the remaining length of the element, including the grippable head end to be employed for another fracture-mending procedure, as described above. In addition, configuring the surfaces of the semi-cylindrical depressions of the two plates of the chuck as threaded surfaces allows the chuck to be used to 'rethread' a rod-shaped fixation element, as desired.

Thus, the fixation element can be cut to appropriate lengths at bone surface level, allowing its use in areas previously restricted by overlying vital soft tissue structures (e.g. tendon bone beds, or ligament and capsular attachment points). Such bone growth may be modified further by commercial or autograft additions of substances designed to promote such growth.

As pointed out above, such stable 'touching' is all that is necessary for the fracture to mend. In fact, it is not necessary that the two bone surfaces actually touch one another, but may be slightly separated (e.g., in a range on the order of less than one millimeter), as the natural behavior of the bone marrow is to stimulate growth tissue sites that project toward and attach with those of the opposing surface of the other bone section. Since the fixation element is preferably made of resorbable material, it is eventually replaced by bone tissue in the course of the two bone sections growing together in this 'just touching' position.

While I have shown and described several embodiments in accordance with the present invention, it is to be understood that the same is not limited thereto but is susceptible to numerous changes and modifications as are known to a person skilled in the art, and I therefore do not wish to be limited to the details shown and described herein, but intend to cover all such changes and modifications as are obvious to one of ordinary skill in the art.

What is claimed:

1. A method for repairing a bone fracture comprising the steps of:

(a) providing a cannulated generally longitudinally configured compression decompression fixation element that is flexible about at least a longitudinal axis thereof; and (b) inserting said fixation element through a first bone section on one side of said bone fracture and along a path that intersects said bone fracture, said path passing into a second bone section on a second side of said bone fracture, so as to impart a compression decompression force between said first bone section and said second bone section at said bone fracture, said path being such as to bias said fixation element in a direction transverse to said longitudinal axis thereof, and thereby urge said first bone section apart from said second bone section in a manner that opposes said soft tissue compression force between said first bone section and said second bone section at said bone fracture, and thereby maintains said first and second bone sections or more and soft tissues in a prescribed spatial relationship at said fracture that provides for mending between said first and second bone sections with minimal compression therebetween, or to penetrate a second bone fragment.

2. A method according to claim 1, wherein said fixation element contains a material that resorbs on contact with body fluid.

3. A method according to claim 1, wherein said fixation element has a hollow passageway along said longitudinal axis.

4. A method according to claim 1, wherein said fixation element intersects a portion of bone material of said second bone section on said second side of said bone fracture that deflects a forward end of said fixation element and biases said fixation element in said direction transverse to said longitudinal axis thereof or penetrates said second section of bone material.

5. A method according to claim 1, wherein said path intersects said bone fracture at an acute angle.

6. A method according to claim 1, wherein said first bone section comprises a metaphyseal bone region.

7. A method according to claim 1, wherein said fixation element has a textured surface that causes said fixation element to maintain a prescribed impingement upon said first and second bone sections, and thereby said fixation element from being displaced from an established insertion location and orientation within said bone sections.

8. A method according to claim 1, wherein said fixation element is configured as one of a longitudinal rod, shaft, nail and pin having a surface which contains a plurality of raised regions.

9. A method according to claim 8, wherein said raised regions include at least one of threads, bumps, ridges and rings.

10. A method according to claim 1, wherein said fixation element has grippable head portion, and wherein step (b) comprises securing a chuck about a forward portion of said fixation element in the vicinity of first bone section, and rotating said chuck in association with rotation of said grippable head portion so as to prevent build up of torsion forces in said fixation element.

11. A method according to claim 1, wherein step (b) comprises inserting an impediment into said second bone section that intersects said path, so that a forward end of said fixation element abuts against said impediment in said second bone section, and allows said fixation element to be torqued away from said fracture, and thereby relieve compression between said first and second bone sections.

12. A method for repairing a bone fracture comprising the steps of:
  (a) inserting a flexible cannulated compression decompression fixation element having a textured surface and being flexible about a longitudinal axis thereof, along a path through a first bone section on one side of said bone fracture and into a second bone section on a second side of said bone fracture, so as to optimize mutual separation between said first bone section and said second bone section at said bone fracture or to penetrate said second bone at an acute angle; and
  (b) biasing said flexible cannulated compression decompression fixation element in a direction transverse to said longitudinal axis thereof, thereby urging said first bone section apart from said second bone section in a manner that opposes soft tissue compression or laxity between said first bone section and said second bone section at said bone fracture, while maintaining said first and second bone sections in a spatial relationship at said fracture that facilitates mending between said first and second bone sections with minimal deforming compression therebetween.

13. A method according to claim 12, wherein step (b) comprises inserting said fixation element along a guide path containing a guide element passing through said hollow passageway of said fixation element and intersecting a location in said second bone section that deflects a forward end of said fixation element in said direction transverse to said longitudinal axis thereof to abut against an impediment within said second bone section that intersects said path, and allow said fixation element to be torqued away from said fracture, and thereby relieve compression between said first and second bone sections.

14. A method according to claim 13, wherein said fixation element contains a material that resorbs on contact with body fluid, and has a hollow passageway along said longitudinal axis, making said fixation element flexible about said longitudinal axis thereof.

15. A method according to claim 12, wherein said fixation element has grippable head portion, and wherein step (b) comprises securing a chuck about a forward portion of said fixation element in the vicinity of first bone section, and rotating said chuck in association with rotation of said grippable head portion so as to prevent build up of torsion forces in said fixation element.

16. An orthopaedic surgical appliance for use in the repair of a bone fracture comprising:
  a cannulated compression decompression fixation element having a hollow passageway and a textured surface sufficient to maintain said fixation element at a prescribed impingement upon said first and second bone sections, and thereby prevent said fixation element from being displaced from an established insertion location and orientation within said first and second bone sections, said fixation element being flexible about a longitudinal axis thereof, so as to be insertable along a path through a first bone section on one side of said bone fracture and into a second bone section on a second side of said bone fracture, so as to optimize mutual separation between said first bone section and said second bone section at said bone fracture or to be incident upon said second bone at an acute angle; and
  an impediment insertable into said second bone section at a location that intersects said path and is abutted by a forward end of said fixation element within said second bone section, so as to provide a leverage location from which said fixation element may be torqued away from said fracture, and relieve compression between said first and second bone sections.

17. An orthopaedic surgical appliance according to claim 16, further including a guide element insertable along said path and passing through said hollow passageway of said fixation element and intersecting a location in said second bone section that deflects a forward end of said fixation element in said direction transverse to said longitudinal axis thereof to abut against said impediment within said second bone section.

18. An orthopaedic surgical appliance according to 16, wherein said fixation element contains a material that resorbs on contact with body fluid.

19. An orthopaedic surgical appliance according to claim 16, wherein said fixation element has a grippable head portion, and further including a chuck that is securable about a forward portion of said fixation element in the vicinity of first bone section, so that rotation of said chuck in association with rotation of said grippable head portion prevents build up of torsion forces in said fixation element.

20. An orthopaedic surgical appliance according to claim 16, wherein said fixation element is configured in the shape of one of a longitudinal rod, shaft, nail and pin, and wherein said textured surface contains a plurality of raised regions.

* * * * *